US008852116B2

United States Patent
Shinba (10) Patent No.: US 8,852,116 B2
(45) Date of Patent: Oct. 7, 2014

(54) PSYCHIATRIC SYMPTOM AND PSYCHIATRIC DISORDER ONSET RISK EVALUATION METHOD AND EVALUATOR USING HEART RATE VARIABILITY INDEX

(71) Applicants: GM3 Co., Ltd., Tokyo (JP); Toshikazu Shinba, Tokyo (JP); Koujirou Tokuhara, Tokyo (JP)

(72) Inventor: Toshikazu Shinba, Tokyo (JP)

(73) Assignees: GM3 Co., Ltd. (JP); Toshikazu Shinba (JP); Koujirou Tokuhara (JP)

( * ) Notice: Subject to any disclaimer, the term of this patent is extended or adjusted under 35 U.S.C. 154(b) by 0 days.

(21) Appl. No.: 14/073,909

(22) Filed: Nov. 7, 2013

(65) Prior Publication Data

US 2014/0058279 A1 Feb. 27, 2014

(30) Foreign Application Priority Data

May 8, 2012 (JP) .................................. 2012-106955

(51) Int. Cl.
*A61B 5/16* (2006.01)
*A61B 5/00* (2006.01)
*A61B 5/024* (2006.01)

(52) U.S. Cl.
CPC ................. *A61B 5/16* (2013.01); *A61B 5/4058* (2013.01); *A61B 5/165* (2013.01); *A61B 5/7275* (2013.01); *A61B 5/7246* (2013.01); *A61B 5/7278* (2013.01); *A61B 5/02405* (2013.01)
USPC ........................................................ 600/508

(58) Field of Classification Search
USPC ......................................... 600/508, 515–518
See application file for complete search history.

(56) References Cited

U.S. PATENT DOCUMENTS

2007/0021675 A1    1/2007  Childre et al.

FOREIGN PATENT DOCUMENTS

| JP | 3250474 B2 | 11/2001 |
| JP | 2005218595 A | 8/2005 |
| JP | 2008229233 A | 10/2008 |
| JP | 2009207763 A | 9/2009 |
| JP | 4487015 B1 | 6/2010 |
| JP | 4568825 B2 | 8/2010 |
| JP | 4637963 B1 | 2/2011 |

OTHER PUBLICATIONS

Akselrod et al.: Hemodynamic regulation: investigation by spectral analysis; (American Journal of Physiology, 249: H867-875, 1985).
Malik, M. Heart rate variability: Standards of measurement, physiological interpretation, and clinical use. Circulation 93, 39 pgs., 1996.

*Primary Examiner* — Amanda Patton
(74) *Attorney, Agent, or Firm* — Schmeiser, Olsen & Watts LLP (57) ABSTRACT

An evaluator includes a heart rate variability analyzer A having a heart rate measuring instrument, a heartbeat interval measuring instrument, a frequency analyzer, a sympathetic/parasympathetic nervous system index analyzer, and a psychiatric symptom/psychotic disorder onset risk calculator, and a random number generation analyzer having a random number input unit, a random number score calculation unit, and a display unit. Frequency analysis of a heart rate measurement and a heartbeat interval measurement of a subject is performed to determine a high-frequency index, a low-frequency index and a ratio therebetween.

4 Claims, 4 Drawing Sheets

Fig.4

PSYCHIATRIC SYMPTOM AND PSYCHIATRIC DISORDER ONSET RISK EVALUATION METHOD AND EVALUATOR USING HEART RATE VARIABILITY INDEX

FIELD OF TECHNOLOGY

The following relates to a psychiatric symptom and psychiatric disorder onset risk evaluation method and evaluator using a heart rate variability index.

BACKGROUND

The beating rate of a heart is always changed. In other words, the interval between heartbeats is extended and shortened in a repetitive manner. This is the heart rate variability, and the change thereof is subjected to control of the autonomic nervous system. The autonomic nervous system is composed of a sympathetic nervous system which arouses and strains the mind and body, and a parasympathetic nervous system which sedates and rests the same. Various physiological and pharmacological researches beginning at the research by Akselrod et al. (American Journal of Physiology, 249: H867-875, 1985) have found that the component of 0.04 to 0.15 hertz (Low Frequency: LF) of the heart rate variability reflects both activities of the sympathetic nervous system and the parasympathetic nervous system, while the component of 0.15 to 0.4 hertz (High Frequency: HF) thereof reflects the activity of the parasympathetic nervous system. In addition, using the ratio of LF/HF as an index of the sympathetic nervous system activity is practiced by a number of researchers.

These indices are standardized by the European Society of Cardiology, and the like, and are used as a guideline (Malik, M. Heart rate variability: Standards of measurement, physiological interpretation, and clinical use. Circulation 93, 1043-1065, 1996), being utilized for pathology analysis of heart diseases.

In recent years, various attempts to utilize the heart rate variability for evaluation of the mental status have been made, and various methods for accurately and conveniently measuring the heart rate variability have been proposed. For example, in Japanese Patent Publication No. 4568825 (Patent Document 1), in consideration of the fact that the parasympathetic nervous system component of a heart rate variability is closely related to the breathing rhythm, a method for calculating the index of the parasympathetic nervous system activity on the basis of the length of one breath is proposed.

In Japanese Patent Publication No. 4487015 (Patent Document 2), in consideration of the fact that the LF and HF may greatly vary depending upon the individual difference or the difference produced in repetitive recording, it is proposed that a coefficient of variation of RR interval (CVRR) should be incorporated in the mathematical expression to indicate the sympathetic nervous system activity and the parasympathetic nervous system activity with new indices, i.e., (CVRR×LF/(LF+HF)) and (CVRR×HF/(LF+HF)), respectively, and in Japanese Unexamined Patent Publication No. 2008-229233 (Patent Document 3), a short-time Fourier method which uses heartbeat data obtained through as small as 100 beats for analysis is proposed.

In addition, a method for accurately analyzing the mental state through the analysis of the combination with or correlation to another index, such as a brain wave or a blood pressure, is also proposed. For example, in Japanese Patent Publication No. 4410234 (Patent Document 4) and Japanese Unexamined Patent Publication No. 2009-207763 (Patent Document 5), a method is disclosed which analyzes the correlation by determining the pattern of breathing, the rhythm of blood pressure change, the coefficient of R-wave amplitude in an electrocardiograph, and the like in addition to the heart rate variability.

However, while these methods disclosed in the above-mentioned patent documents contribute to the progress of the measuring or analyzing method, these patent documents have no specific disclosure about how to utilize the invention for analysis or diagnosis of the change in mental status or pathology of a psychiatric disorder. Thus, there has been no preferred method for implementing utilization of a heart rate variability index in analysis, diagnosis, or prevention of the change in pathology of a psychiatric disorder, however, there are available the following patent documents which intend implementation thereof, and many of them focus on evaluation of the stress state.

The change in heart rate variability in the stress state can be a change which is a healthy reaction per se, and therefore, the change is not the same as that related to a psychiatric disorder or the risk of onset thereof, however, there are no prior art documents which mention this point.

The invention disclosed in Japanese Patent Publication No. 4637963 (Patent Document 6) uses heart rate variability indices before and after deep breathing and from the difference, checks for health state. It is a publicly known fact that the rhythm of breathing can have an influence on the heart rate variability. The heart rate variability index for the parasympathetic nervous system depends on the rhythm of breathing. The health checking method using the rhythm of breathing is meaningful, however, it is supposed that the method perhaps focuses on the reaction persistence of the parasympathetic nervous system to the breathing. Also about depression, the document states that "it can be simply and instantaneously made clear that there is a high possibility of the subject having depression", however, there have been no clinical observations proving that utilization of the heart rate variability due to the breathing load is useful for identification of depression. It is supposed that, for evaluation of the psychiatric symptom and the depression, a mental load should be imposed on the subject.

Further, the invention disclosed in Japanese Patent Publication No. 4238321 imposes a mental arithmetic stress on the subject, and from the change in heart rate variability power value and frequency, verifies the existence of a stress. However, in the patent document disclosing this invention, it is stated that "an average power value of 0.2 Hz or under is calculated", but if an average is determined for this frequency band, the average involves both of the sympathetic nervous system component and the parasympathetic nervous system component, thereby the autonomic nervous system evaluation cannot be accurately performed, which is a problem.

Further, for the invention disclosed in Japanese Patent Publication No. 4238321, it is stated that "when the average power frequency is increased to or over a prescribed value with respect to the criterion value, it is judged that the subject is feeling an emotional stress", however, there is no discussions about a fact that responding to a stressor is different from falling in a pathologic stress condition, which is a problem. In other words, it is often a healthy activity that the autonomic nervous system reacts to a mental load, while, in a pathologic stress condition, such reaction is not caused, is excessive, is delayed or disordered, but the invention is lacking consideration about this point.

Further, with the invention disclosed in Japanese Patent Publication No. 3250474, the heart rate and the indices of the sympathetic and parasympathetic nervous system activities are recorded in the resting state and the task performing state, the data being expressed as a distribution graph, and determines that, if the data for one state is overlapped on that for the other in many places, the subject has a stress.

However, this method gives indices of the sympathetic and parasympathetic nervous system activities on the basis of the dispersion of change in heart rate, such indices involving the activities of both sympathetic nervous system and parasympathetic nervous system, however, both of these activities have meanings in the contradictory directions, i.e., positive and negative ones concerning the mental status, thereby utilization of the indices having a mixture of those presents a problem. In addition, utilizing the unitary evaluation method, which is based on only the overlapping of distribution data in the resting state and that in the task performing state, for evaluation of a complicated mental status is difficult, as with the inventions mentioned above.

The heart rate fluctuation and other various autonomic nervous system activities are carried out under the control of the controlling center in the brain stem, however, it is known that they are heavily influenced by the mental status. The modern society gives much stress, and the incidence rate of the psychiatric disorder, such as depression, the number of employees on administrative leave and that of suicides are being increased. However, the diagnosis of the psychiatric symptom is subjective, and as described above, the early treatment and prevention using an objective index have not yet been put into practical use.

SUMMARY

The present invention has been made in view of such medical and societal situations in which development of an objective evaluation method has been demanded, and it may provide a psychiatric symptom and psychiatric disorder onset risk evaluation method and evaluator using a heart rate variability index that are useful for biologically evaluating the psychiatric symptom through the analysis of the autonomic nervous system activity on the basis of a heart rate variability measurement, and effective for understanding the psychiatric symptom and checking for psychiatric disorder onset risk.

Solution to Problem

The problems of the prior art in the field of heart rate variability analysis are attributable to the fact that there is an individual difference in heart rate variability index value, and that only the measurement in the steady state, such as the resting state, is used for analysis, and found that, in order to analyze an important pathology of psychiatric disorder of the disability of mind to respond in different situations, it is necessary to examine the responsiveness to situation and the ability to control, having completed the present invention.

The invention according to claim 1 to solve the above-mentioned problems provides a method for utilizing a heart rate variability index for diagnosis of a psychiatric disorder or detection of the risk of onset thereof, including:

the task presentation and frequency analysis step at which frequency analysis is performed on a measured heart rate and a measured heartbeat interval of a subject for determining a high-frequency index, a low-frequency index and a ratio therebetween;

the sympathetic nervous system and parasympathetic nervous system index calculation step at which a sympathetic nervous system index and a parasympathetic nervous system index are calculated from the result of the frequency analysis; and the index comparison evaluation step at which the heart rate, sympathetic nervous system index and parasympathetic nervous system index calculated are compared, for evaluation, with threshold values which have been determined from the heart rate, the sympathetic nervous system index, and the parasympathetic nervous system index of a healthy subject that have been previously calculated and stored, the high-frequency index, the low-frequency index, and the ratio therebetween at the frequency analysis step being those which have been obtained through the measurement and frequency analysis in three states, i.e., the resting state, the task performing state, and the resting state after task performance of the subject, respectively, and the threshold values being set so as to reflect the psychiatric disorder and the risk of onset thereof in a multilateral manner for every index in the respective states.

In one embodiment, as the task to be imposed on the subject at the frequency analysis step, a task with which the individual difference in achievement level is small is used, and as the task with which the individual difference in achievement level is small, random number generation is used.

Further, the invention according to claim 4 provides a psychiatric symptom and psychiatric disorder onset risk evaluator, including:

a heart rate variability analyzer and a random number generation analyzer, wherein the heart rate variability analyzer is configured to include a heart rate measuring instrument, a heartbeat interval measuring instrument, a frequency analyzer, a sympathetic/parasympathetic nervous system index analyzer, and a psychiatric symptom/psychotic disorder onset risk calculator, and the random number generation analyzer is configured to include a random number input unit, a random number score calculation unit, and a display unit, the heart rate variability analyzer performing frequency analysis of a heart rate value and a heartbeat interval of a subject that have been measured in the resting state, the task performing state, and the resting state after task performance of the subject, respectively, for calculating a high-frequency index, a low-frequency index, and a ratio therebetween, wherein the psychiatric symptom/psychiatric disorder onset risk calculator includes a storage unit and a comparison unit, the storage unit storing threshold values which have been previously set on the basis of a high-frequency index, a low-frequency index and a ratio therebetween which have been obtained from frequency analysis of a heart rate and a heartbeat interval of a healthy subject that have been measured in the resting state before task performance, the task performing state, and the resting state after task performance, respectively, and the comparison unit comparing the relevant threshold values with the high-frequency index, the low-frequency index and the ratio therebetween of the subject, and depending upon whether the index exceeds the relevant threshold value, whether there is a prescribed psychiatric symptom or not, and the existence of psychosis risk being determined.

Advantageous Effects of Invention

The present invention is as described above, and it reflects the fact that the sympathetic nervous system index and the parasympathetic nervous system index in the task performing state and the resting state after task performance are different from the index in the resting state before task performance, and determines and analyzes the high-frequency index, the low-frequency index, and the ratio therebetween in the resting state, the task performing state, and the resting state after task performance of the subject, respectively, at the frequency analysis step, thereby the relevant data being extremely effective as data for determining whether there is a prescribed psychiatric symptom and evaluating the psychiatric disorder onset risk, and therefore allowing determination of whether there is a psychiatric symptom and evaluation of the psychiatric disorder onset risk to be performed properly.

In addition, as the task to be imposed on the subject at the frequency analysis step, a task with which a difference due to the capability or experience of the subject is not easily produced, and the individual difference in achievement level is small is used, and for this, random number generation is used for example, thereby the data for the high-frequency index, the low-frequency index, and the ratio therebetween in the resting state, the task performing state, and the resting state after task performance of the subject that is used for evaluating the pathological condition being effective data which will not be influenced by the individual difference in task achievement level.

BRIEF DESCRIPTION

DETAILED DESCRIPTION

The method in accordance with the present invention is a method for utilizing a heart rate variability index to make diagnosis of a psychiatric disorder or detection of the onset risk, however, it is a method which analyzes the three distinct conditions of anxiety strain, avolition, and fatigue rather than an unarticulated mind and body sickness which is expressed by a word of stress, and which, in order to allow the analysis thereof, utilizes the data obtained in the three states of the resting state before task presentation, the task performing state, and the resting state after task performance.

In other words, the psychiatric symptom and psychiatric disorder onset risk evaluation method using a heart rate variability index in accordance with the present invention includes:

the task presentation and frequency analysis step at which frequency analysis is performed on a measured heart rate and a measured heartbeat interval of a subject for determining a high-frequency index, a low-frequency index and a ratio therebetween;

the sympathetic nervous system and parasympathetic nervous system index calculation step at which a sympathetic nervous system index and a parasympathetic nervous system index are calculated from the result of the frequency analysis; and the index comparison evaluation step at which the heart rate, sympathetic nervous system index and parasympathetic nervous system index calculated are compared, for evaluation, with threshold values which have been determined from the heart rate, the sympathetic nervous system index, and the parasympathetic nervous system index of a healthy subject that have been previously calculated and stored, the high-frequency index, the low-frequency index and the ratio therebetween at the frequency analysis step being those which have been obtained through the measurement and frequency analysis in the resting state, the task performing state, and the resting state after task performance of the subject, respectively, and the threshold values being set so as to reflect the psychiatric symptom and the psychiatric disorder onset risk.

Figure 2:
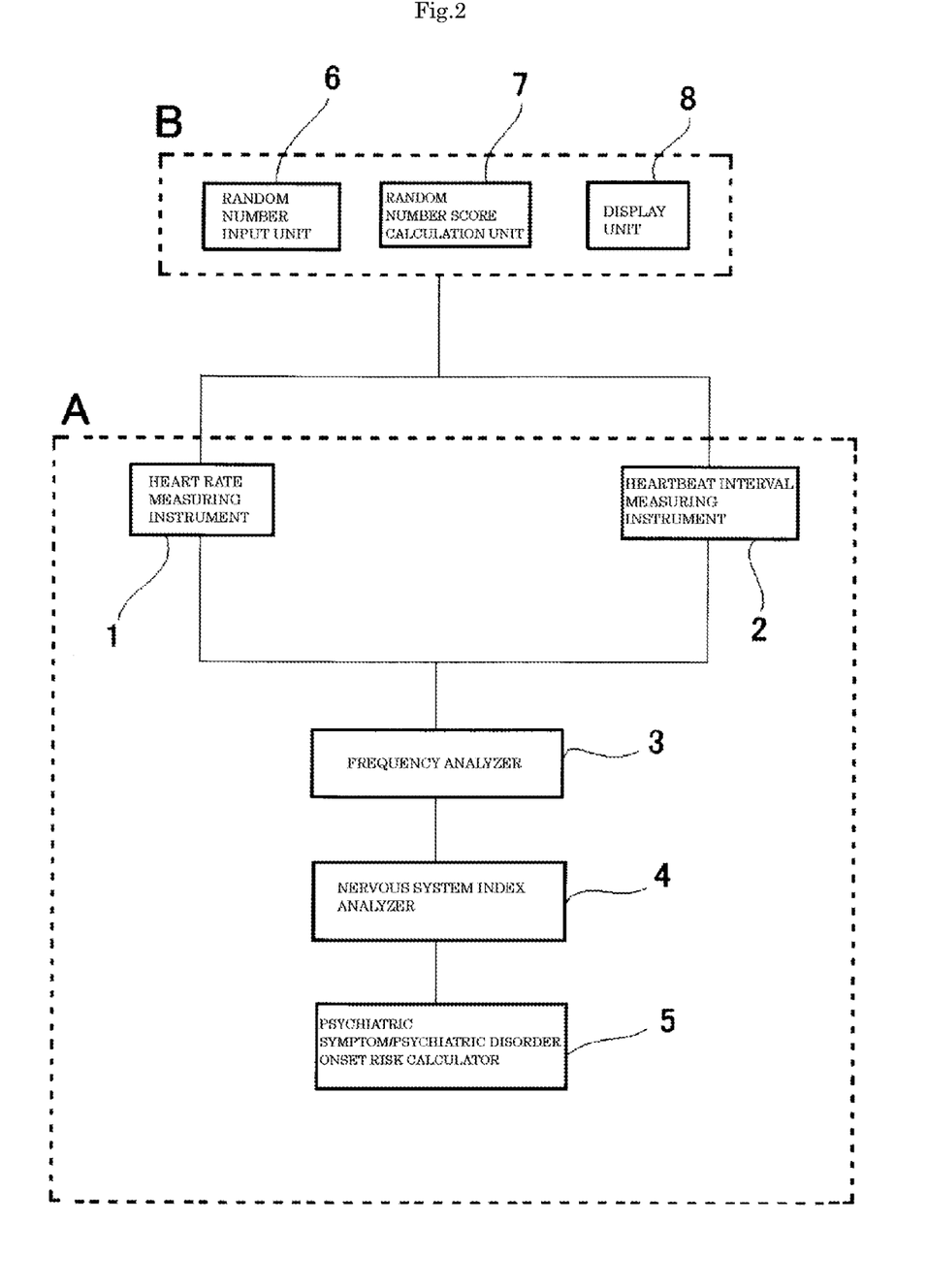
FIG. 2 is a diagram illustrating the configuration of a psychiatric symptom and psychiatric disorder onset risk evaluator.

Further, the psychiatric symptom and psychiatric disorder onset risk evaluator using a heart rate variability index in accordance with the present invention is an evaluator for implementing the above-mentioned method, and as shown in FIG. 2, the evaluator includes a heart rate variability analyzer A, and a random number generation analyzer B, utilizing random number generation as a task to be imposed on a subject. The heart rate variability analyzer A is configured to include a heart rate measuring instrument 1, a heartbeat interval measuring instrument 2, a frequency analyzer 3, a sympathetic/parasympathetic nervous system index analyzer 4, and a psychiatric symptom/psychiatric disorder onset risk calculator 5. In addition, the random number generation analyzer B is configured to include a random number input unit 6, a random number score calculation unit 7, and a display unit 8.

With the heart rate variability analyzer A, the heart rate measuring instrument 1 and the heartbeat interval measuring instrument 2 give a heart rate value and a heartbeat interval measurement for the subject in the resting state, the task performing state, and the resting state after task performance of the subject, respectively. And, with the frequency analyzer 3, frequency analysis of those measurements is performed for calculating a high-frequency index, a low-frequency index and a ratio therebetween.

The psychiatric symptom/psychiatric disorder onset risk calculator 5 includes a storage unit and a comparison unit, the storage unit storing threshold values which have been previously set as criteria for evaluation. These threshold values are set by imposing random number generation on a healthy subject as a task in the same manner as on the subject, making frequency analysis of the heart rate value and the heartbeat interval measurement which have been given in the resting state before task performance, the task performing state, and the resting state after task performance, respectively, to obtain a high-frequency index, a low-frequency index and a ratio therebetween, and, for each of those, referencing an investigational case. And, with the comparison unit in the psychiatric symptom/psychiatric disorder onset risk calculator 5, such threshold values are compared with the high-frequency index, the low-frequency index and the ratio therebetween of the subject, respectively, which have been sent from the sympathetic/parasympathetic nervous system index analyzer 4, and depending upon whether those indices exceed the relevant threshold value, and to what degree they exceed, whether there is a psychiatric symptom or not, and the psychiatric disorder onset risk are evaluated.

Figure 1:
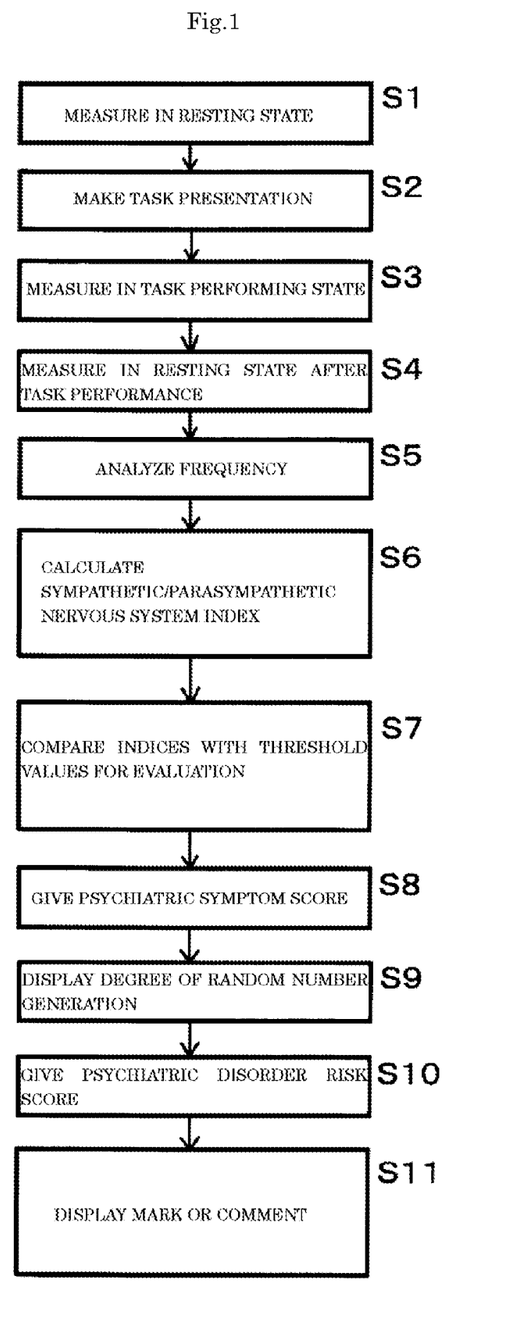
FIG. 1 is a chart illustrating the flow of operation by a psychiatric symptom and psychiatric disorder onset risk evaluation method.

Next, the method in accordance with the present invention will be described in detail in the order of step with reference to the flowchart shown in FIG. 1.

Task Presentation and Frequency Analysis Step

The task presentation and frequency analysis step is a step (composed of step S1 to S5) which performs frequency analysis on the heart rate measurement and the heartbeat interval measurement for the subject to determine the high-frequency index, the low-frequency index and the ratio therebetween. For measuring the heart rate of the subject, an existing heart rate measuring system may be used. In addition, on the basis of the heartbeat interval obtained from an electrocardiograph or a pulse wave, frequency analysis of the heart rate trend data is performed to determine the high-frequency index (HF), the low-frequency index (LF), and the ratio (LF/HF) between both indices, which have been used on various apparatuses up to now. Determining the HF, LF, and LF/HF values in this way has been conventionally performed, and it is known that the HF index reflects the parasympathetic nervous system activity, the LF index reflecting both of the sympathetic and sympathetic nervous system activities, and the LF/HF index the sympathetic nervous system activity.

However, with the method in accordance with the present invention, the high-frequency index, the low-frequency index, and the ratio therebetween are obtained by making frequency analysis (at step S5) of the data which has been measured in the resting state (at step S1), the task performing state (at step S3), and the resting state after task performance (at step S4) of the subject, respectively. And, the performance task to be imposed on the subject at step S2 is preferably a task with which the individual difference in achievement level is small, in other words, a difference due to the capability or experience of the subject is not easily produced (the task, such as mental arithmetic, which is used by the invention disclosed in Patent Document 7: Japanese Patent Publication No. 4238321 provides a great individual difference, thereby there being a possibility that effective data may not be obtained), and thus, it is recommended to use, for example, a random number generation task, however, the task is, of course, not limited to this, and any task equivalent thereto will suffice.

For example, the random number generation task should have a content of "saying numbers of one-digit from 0 to 9 in an order as random as possible". And, the subject is instructed to "do his or her best", being away from the initial relax state. The random number generation itself reflects the degree of attention, and the task performing state is evaluated on the randomness score. For calculating the randomness score, the counting bias and interval bias, the random number generation index, etc. can be used (Shinba et al., Perceptual and Motor Skills 91, 1091-1105, 2000). Before the test, checking for anxiety depression state is performed by the self-filling-in type questionnaire sheet method.

Sympathetic/Parasympathetic Nervous System Index Calculation Step

The sympathetic/parasympathetic nervous system index calculation step (step S6) is a step at which the sympathetic nervous system index and the parasympathetic nervous system index are calculated from the result of the frequency analysis. As described above, with the method in accordance with the present invention, the data is used which has been obtained in the three states, i.e., the resting state, the task performing state, the resting state after task performance. In other words, the heart rate measurement and the heartbeat interval measurement obtained in each of these three states are frequency-analyzed to determine/calculate the three items, i.e., the heart rate (HR), the sympathetic nervous system activity index (LF/HF), and the parasympathetic nervous system activity index (HF), thereby nine indices in total being obtained to be stored for use in evaluation of the pathology, and the like.

Index Comparison Evaluation Step

The index comparison evaluation step (step S7) is a step at which the sympathetic nervous system index and the parasympathetic nervous system index, which have been calculated and stored, are compared, for evaluation, with threshold values which have been determined from the sympathetic nervous system index and the parasympathetic nervous system index of a healthy subject that have been previously calculated and stored. The sympathetic nervous system index and the parasympathetic nervous system index of a healthy subject in this case are also obtained in the same manner as those of the subject by making frequency analysis of the heart rate measurement and the heartbeat interval measurement of the healthy subject that have been obtained in the resting state, the task performing state, and the resting state after task performance, respectively. And, the threshold values, which are previously set as comparison criteria, are set so as to reflect the psychiatric symptom and the psychiatric disorder onset risk (varying depending upon the type of psychiatric disorder).

Figure 3:
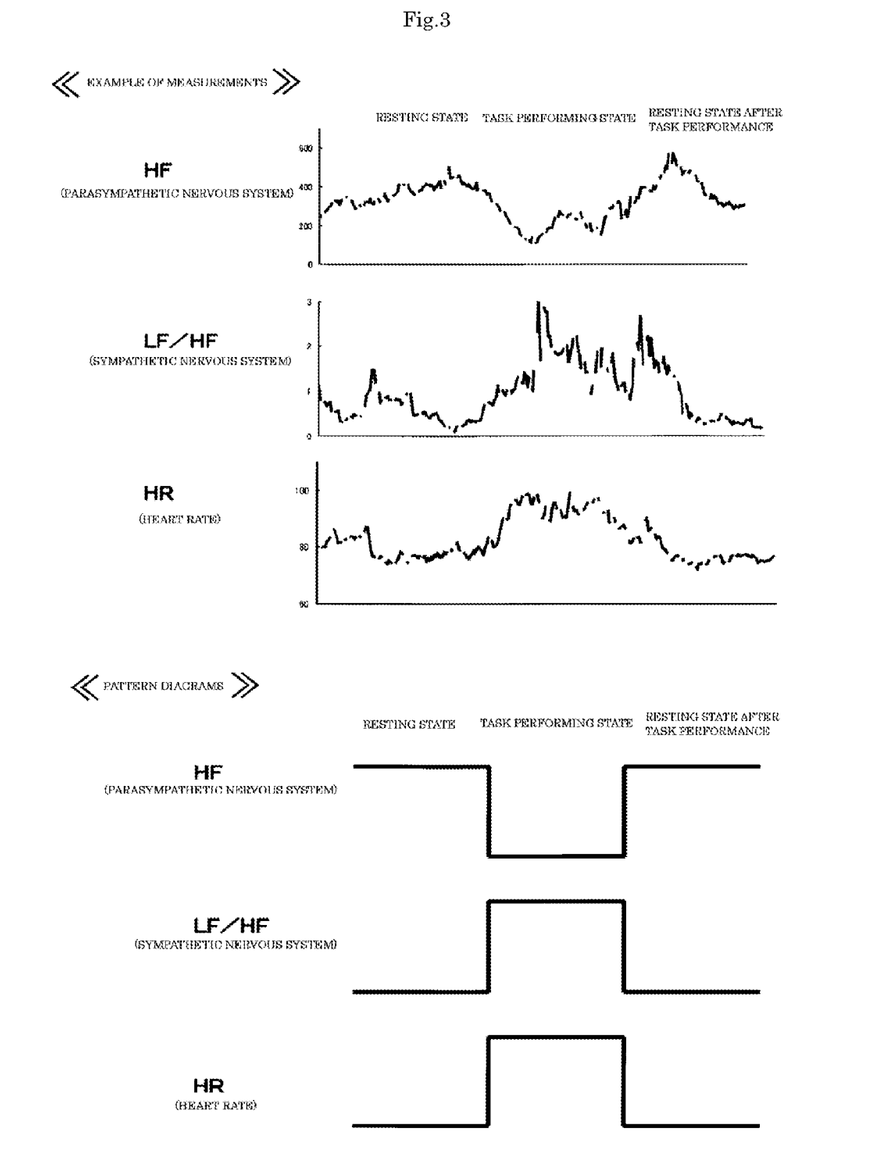
FIG. 3 gives graphs as an example of measurement results and pattern diagrams for a healthy subject illustrating the psychiatric symptom and psychiatric disorder onset risk evaluation method.

The heart rate variability index of a healthy subject is biased in activity balance to the parasympathetic nervous system side in the initial resting state, and in the task performing state, the parasympathetic nervous system index is lowered, while, in the resting state after task performance, the original condition is restored (refer to the example of measurements and the pattern diagrams in FIG. 3). And, if a reaction which is greatly deviated from that in the healthy activity state is recognized, in other words, if the difference from the threshold value exceeds a prescribed value, the condition is detected as an abnormal one. The inventor of the present invention has used the data for fifty healthy subjects and twenty-two depression subjects to obtain a finding which provides a statistically significant difference (FIG. 4), and it is supposed that the method in accordance with the present invention has a high credibility in risk evaluation for the psychiatric disorder including depression.

Figure 4:
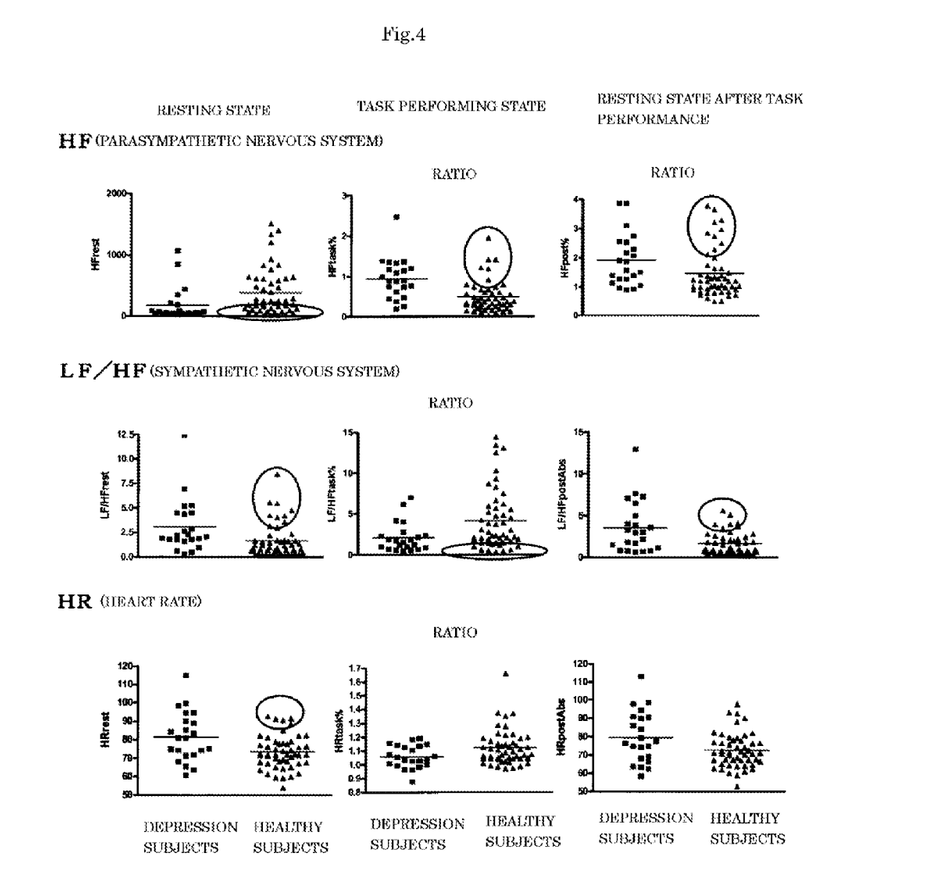
FIG. 4 gives heart rate variability index distribution diagrams illustrating the psychiatric symptom and psychiatric disorder onset risk evaluation.

For example, FIG. 4 gives an example of utilization of the evaluation method for depression, showing distributions of the data for nine different heart rate variability indices of depressives (at left) and healthy subjects (at right). Among the nine graphs, those to which the word "ratio" is attached use the ratio between indices (rel-rest), which is later described in the paragraph [0038]. The data as a whole exhibits a clear difference between the group of depressives and that of healthy subjects, however, the data distribution in a portion of the graph for the group of healthy subjects that is circled is similar to that in the corresponding portion of the graph for the group of depressives, and is evaluated to provide a possible risk of depression onset. For another type of psychiatric disorder, the method for utilizing the indices is altered for an optimum result.

As described above, the method in accordance with the present invention uses the nine heart rate variability indices in total, i.e., the HF, LF/FH, and heart rate (HR) in the three states, i.e., the resting state (abbreviated to "rest"), the task performing state (abbreviated to "task"), and the resting state after task performance (abbreviated to "post") to evaluate the autonomic nervous system imbalance for performing diagnosis of a stress related psychiatric disorder, such as depression, and clarifying the risk thereof.

The nine different indices can be further utilized as the absolute value (abbreviated to "abs") and the ratio or difference in relation to the index in the resting state (abbreviated to "rel-rest"), or the ratio or difference in relation to the index in the task performing state (abbreviated to "rel-task"). For example, the nine different indices can be used, being expanded to the following eighteen different indices:

1) HFrest-abs,
2) HFtask-abs,
3) HFtask-rel-rest,

4) HFpost-abs,
5) HFpost-rel-rest,
6) HFpost-rel-task,
7) LF/HFrest-abs,
8) LF/HFtask-abs,
9) LF/HFtask-rel-rest,
10) LF/HFpost-abs,
11) LF/HFpost-rel-rest,
12) LF/HFpost-rel-task,
13) HRrest-abs,
14) HRtask-abs,
15) HRtask-rel-rest,
16) HRpost-abs,
17) HRpost-rel-rest, and
18) HRpost-rel-task.

The value in the resting state expresses the state in which the subject is relaxed; the value in the task performing state expresses the reaction upon the stress being imposed; and the value in the resting state after task performance depicts the change through which the nervous system restores the relaxed state, these values being used for evaluation of the anxiety strain state, the avolition, and the fatigue or somatic symptom, respectively. FIG. 3 gives one example of using the values, and in this example, from the data obtained by continuously determining the HF value and LF/HF value, and HR value every 2 seconds for approx. 100 seconds in the resting state, for approx. 100 seconds in the random number generation task performing state, and for approx. 100 seconds in the resting state after task performance, average values were calculated for the above-mentioned three respective time periods for use as the indices. In the example given in FIG. 3, because the data was analyzed by the maximum entropy method every 2 seconds for 1 minute, the numerical values obtained over 1 minute from 30 seconds after the start of the respective states were averaged.

For example, threshold values of a, b, c, d, e, f, and g (which are given in the expression of HFrest<a, HFtask-rel-rest>b, HFpost-rel-rest>c, LF/HFrest>d, LF/HFtask-rel-rest<e, LF/HFpost-abs>f, and HRrest>g, respectively) are set, and if the index concerned meets the relevant expression, a psychiatric symptom score is given as an observation (at step S8). Such psychiatric symptom scores can be used alone or in combination. The threshold values are determined from the difference in data between the healthy subject and the subject.

Each of the psychiatric symptom score constituted by a combination of the above-mentioned heart rate variability index scores, the questionnaire sheet score, and the random number generation score, or a combination of these is used as a psychiatric disorder risk score (at step S8 to step S10). If the psychiatric disorder risk score exceeds a certain threshold value, it is determined that there is a high risk that the subject may contract a disease. The psychiatric symptom score or the psychiatric disorder risk score may be expressed as a mark or a comment for use as a result of measurement (at step S11).

The present invention relates to a method and apparatus which utilize a heart rate variability index for diagnosis of a psychiatric disorder, such as depression, or detection of the risk of onset thereof, however, the present invention has been made on the basis of the finding of the inventor of the present invention that "the sympathetic nervous system indices and the parasympathetic nervous system indices in the task performing state and the state after task performance are different from the indices in the resting state before task performance", and until now there have been made no approaches from such viewpoint. In case where a conventional heart rate variability index which has not been grounded on such an approach is used for evaluation, only the value obtained in one state, such as the resting state, is mainly used, and therefore, in order to analyze an important pathology of psychiatric disorder of disability to respond to a change, it would become necessary to examine the responsiveness to situation and the ability to control.

The method in accordance with the present invention divides the sympathetic nervous system activity index and the parasympathetic nervous system activity index into the basic value in the resting state, the reaction value in the task performing state, and the recovery value in the resting state after task performance for analysis, and evaluates the pathological condition in the respective three states, while it offers another advantage that the somatic symptoms, such as anxiety strain, avolition, and fatigue, which are a plurality of aspects of the psychiatric disorder, such as depression, anxiety disorder, and stress disorder, can be analyzed in separate and multilateral manners.

Hereinabove, the present invention has been explained in detail to some extent, and about the most preferred embodiment, however, since it is obvious that a wide range of different embodiments can be made without departing from the spirit and scope of the present invention, it is to be understood that the present invention is not limited to the specific embodiments thereof except as defined in the appended claims.

REFERENCE SIGNS LIST

The reference sign A denotes a heart rate variability analyzer; B a random number generation analyzer; 1 a heart rate measuring instrument; 2 a heartbeat interval measuring instrument; 3 a frequency analyzer; 4 a sympathetic/parasympathetic nervous system index analyzer; 5 a psychiatric symptom/psychiatric disorder onset risk calculator; 6 random number input unit; 7 a random number score calculation unit; and 8 a display unit.

The invention claimed is:

1. A method for utilizing a heart rate variability index for diagnosis of a psychiatric disorder or detection of the risk of onset thereof, comprising:
  a task presentation and frequency analysis step at which a frequency analysis is performed on a measured heart rate and a measured heartbeat interval of a subject for determining a high-frequency index, a low-frequency index, and a ratio therebetween;
  a sympathetic nervous system and parasympathetic nervous system index calculation step at which a sympathetic nervous system index and a parasympathetic nervous system index are calculated from a result of the frequency analysis; and
  an index comparison evaluation step at which the heart rate, the sympathetic nervous system index and parasympathetic nervous system index calculated are compared, for evaluation, with threshold values which have been determined from the heart rate, the sympathetic nervous system index, and the parasympathetic nervous system index of a healthy subject that have been previously calculated and stored,
  wherein the high-frequency index, the low-frequency index, and the ratio therebetween at said frequency analysis step are obtained through the measurement and frequency analysis in a resting state, a task performing state, and a resting state after task performance of the subject;
  wherein the threshold values being set so as to reflect the psychiatric symptom and the psychiatric disorder onset risk in a multilateral manner for every index in the respective states.

2. The method according to claim 1, wherein, as the task to be imposed on the subject at the frequency analysis step, a task with which the individual difference in achievement level is small is used.

3. The method according to claim 2, wherein, as the task with which the individual difference in achievement level is small, a random number generation is used.

4. A psychiatric symptom and psychiatric disorder onset risk evaluator, comprising:
- a heart rate variability analyzer and a random number generation analyzer;
- wherein the heart rate variability analyzer is configured to include a heart rate measuring instrument, a heartbeat interval measuring instrument, a frequency analyzer, a sympathetic/parasympathetic nervous system index analyzer, and a psychiatric symptom/psychotic disorder onset risk calculator;
- wherein the random number generation analyzer is configured to include a random number input unit, a random number score calculation unit, and a display unit,
- wherein the heart rate variability analyzer performing frequency analysis of a heart rate value and a heartbeat interval of a subject that have been measured in the resting state, the task performing state, and the resting state after task performance of the subject, respectively, for calculating a high-frequency index, a low-frequency index, and a ratio therebetween;
- wherein the psychiatric symptom/psychiatric disorder onset risk calculator includes a storage unit and a comparison unit;
- wherein the storage unit storing threshold values which have been previously set on a basis of a high-frequency index, a low-frequency index and a ratio therebetween which have been obtained from frequency analysis of a heart rate and a heartbeat interval of a healthy subject that have been measured in the resting state before task performance, the task performing state, and the resting state after task performance, respectively;
- wherein the comparison unit comparing the relevant threshold values with the high-frequency index, the low-frequency index and the ratio therebetween of the subject, and depending upon whether the index exceeds the relevant threshold value, whether there is a prescribed psychiatric symptom or not, and the existence of psychosis risk being determined.

* * * * *